US007662611B2

(12) United States Patent
Schmidt et al.

(10) Patent No.: US 7,662,611 B2
(45) Date of Patent: Feb. 16, 2010

(54) APPARATUS AND METHOD FOR IN VITRO STORAGE OF A CORNEA

(75) Inventors: Rolf A. Schmidt, Mohnton, PA (US); David B. Soll, Ambler, PA (US); Richard C. Pauley, Sinking Spring, PA (US)

(73) Assignee: Cleo Cosmetic and Pharmaceutical Company, LLC, Ambler, PA (US)

(*) Notice: Subject to any disclaimer, the term of this patent is extended or adjusted under 35 U.S.C. 154(b) by 747 days.

(21) Appl. No.: 11/259,516

(22) Filed: Oct. 26, 2005

(65) Prior Publication Data

US 2006/0110721 A1 May 25, 2006

Related U.S. Application Data

(60) Provisional application No. 60/622,234, filed on Oct. 26, 2004.

(51) Int. Cl.
*A01N 1/00* (2006.01)

(52) U.S. Cl. .................. 435/284.1; 435/307.1; 206/5.1; 606/151; 24/455; 292/256.6; 292/256.61; 292/256.63; 359/819

(58) Field of Classification Search .............. 435/284.1, 435/307.1; 206/5.1; 606/151; 24/455; 292/256.6, 292/256.61, 256.63; 359/819
See application file for complete search history.

(56) References Cited

U.S. PATENT DOCUMENTS

| | | | |
|---|---|---|---|
| 4,744,481 | A | 5/1988 | Morgan, Jr. |
| 4,844,242 | A | 7/1989 | Chen et al. |
| 4,860,885 | A | 8/1989 | Kaufman et al. |
| 5,166,048 | A | 11/1992 | Soll et al. |
| 2005/0149055 | A1 | 7/2005 | Briday et al. |

FOREIGN PATENT DOCUMENTS

| | | |
|---|---|---|
| EP | 0 262 766 | 4/1988 |
| EP | 1 109 007 | 6/2001 |

*Primary Examiner*—Jill Warden
*Assistant Examiner*—Jameson Q Ma
(74) *Attorney, Agent, or Firm*—Panitch Schwarze Belisario & Nadel LLP

(57) ABSTRACT

A fixture and method is provided for in vitro storage of a cornea. The fixture includes a platform having a corneal-sceral rim receiving surface, a clamp having a mating surface for the cornel-scleral rim and handles. A locking mechanism is provided to secure a donor cornea between the clamp and platform. The combination cornea, platform and clamp are placed in a storage unit having a fluid preservation media. In one embodiment, the storage unit includes a vial having an optically clear closed end and an opened end. A lid is secured to the open end of the vial and engages the handles in order to stabilize the clamped cornea within the vial.

28 Claims, 7 Drawing Sheets

10
20
14
12

APPARATUS AND METHOD FOR IN VITRO STORAGE OF A CORNEA

CROSS REFERENCE TO RELATED APPLICATION

This application claims the benefit of U.S. Provisional Application No. 60/622,234, filed Oct. 26, 2004.

FIELD OF INVENTION

This invention relates to an apparatus and a method for the use and transplantation of human and animal corneas. In particular, it relates to the in vitro storage, securing, testing, preservation, and transportation of the corneas for use in medical and scientific procedures and research.

BACKGROUND

Typical organ transplantation and storage usually requires cumbersome and somewhat inefficient apparatus. Often the individuals transporting human or animal organs employ large containers, packing materials and other items useful for storage of the organ. For example, such containers include: moisture resistant containers, plastic liners and/or Styrofoam crates. While these devices often provide stability and support for the organ, the bulkiness and lack of mobility, limit the functionality of the storage devices. Moreover, in cases where the organs are particularly smaller, such as corneas, these bigger storage units often fail to provide sufficient support to the organ, which increases the risk of damage to the organ during transport and also at the time of retrieval for a contemplated surgical procedure.

Prior art attempted to address the issues associated with smaller organs by using smaller size containers to insert the organs. The smaller containers provided easier and more efficient transportation, but did not provide any easier access and still failed to provide complete support for the organ. These smaller containers often made retrieval of these donor corneas more difficult at the time of the surgical procedure.

SUMMARY OF THE INVENTION

This invention offers an alternative to the more traditional approaches to organ transportation and storage. In particular, the invention relates to the transportation and storage of an animal or human cornea.

In one embodiment of the invention, a ring or platform has a receiving surface upon which the donor cornea rests. The platform is stabilized by legs connected to the bottom side of the platform. The platform is designed so that a retainer or locking mechanism can be snapped onto the platform, trapping the cornea, with simple downward pressure.

The outside diameter of the platform is sized to accommodate a 13-16 mm diameter donor corneal-scleral unit. The inside diameter is sized to allow viewing of the endothelial layer of the cornea, the average diameter of which is approximately 11-12 mm. Essentially, the cornea sits on the upper surface of the platform, which also functions as part of the securing feature of the invention, by engaging a clamp and holding the cornea in position.

The clamp attaches to the platform to hold the cornea in place. In this one embodiment, the clamp is generally cylindrical in shape and the cylinder has side portions that include cutaways. The cutaways provide the ability to flex the clamp and allow the movement of preservation media, which in one embodiment is a specialized cornea tissue preservative solution, into and out of the cylinder. The bottom side of the clamp includes a mating surface that is a split ring with two halves and a locking mechanism, which consists of two pawls. When the clamp is placed above the receiving surface for mating, the pawls attach on the bottom side of the receiving surface when the clamp is in the open position and the ring halves are spread apart. Each pawl then overlays, but not does not lie on top of, the receiving surface, and secures the clamp, the platform and the cornea. Ultimately, the cornea lies on the receiving surface, in between the receiving surface and the two halves of the mating surface.

In another embodiment, the cornea receiving surface and the cornea mating surface are located towards a generally more central location of the apparatus. This further embodiment may provide the locking mechanism displaced downwardly away from the cornea receiving and mating surfaces. The mating surface is generally annular but it may not take the form of a split ring configuration. A stepped web portion may extend around at least a portion of the mating surface, and may include notches in the stepped web portion.

In addition, a storage unit is provided, which, in one embodiment, is a glass or plastic vial into which an operator places the clamp and platform combination. The vial is filled with the preservation media and, since the vial is transparent, the cornea can be seen in the vial. The top of the vial has threads that engage a lid. The lid has an inside, outside, top and bottom and has internal threads that start at the bottom interior of the lid and go half way to the top of the lid. The lid has a flange protruding downwards from the top of the inside of the lid. The flange aids in the stabilization and securitization of the clamp-platform combination by engaging the top of the clamp so that the top of the clamp sits in the interior of the lid.

DETAILED DESCRIPTION

Figures 1, 2:
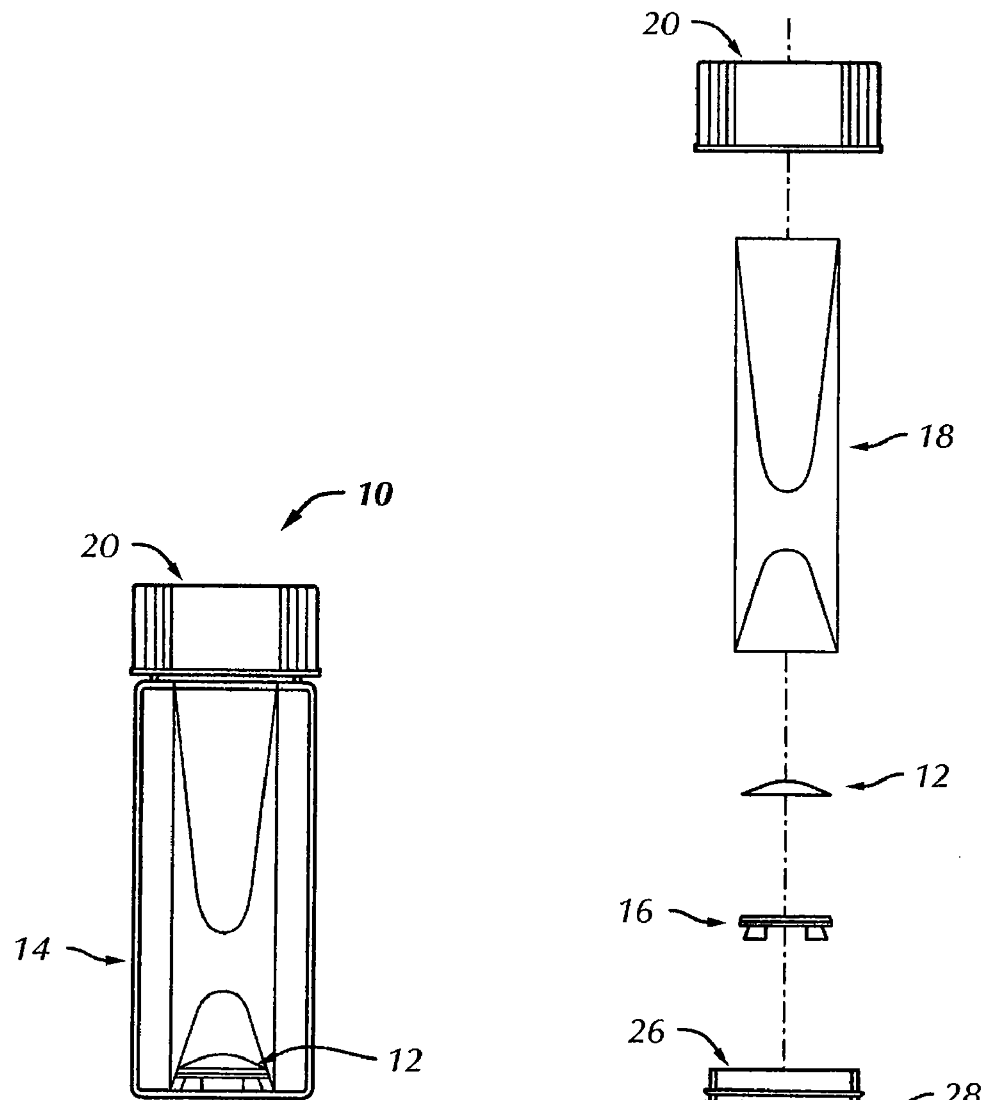
FIG. 1 is a perspective view of the apparatus containing a donor cornea, in accordance with a first embodiment of the present invention.
FIG. 2 is an exploded view of the apparatus shown in FIG. 1.

FIG. 1 is a perspective view of the fixture 10 containing a donor cornea 12 in accordance with one embodiment of the present invention. FIG. 2 is an exploded view of the fixture and donor cornea of FIG. 1. FIG. 2 includes a vial 14, base 16, donor cornea 12, combination clamp and handle 18 and a lid 20. The vial 14 includes a cylindrical side wall 22, an optically clear closed end 24, an opened end 26 having external threads 28.

Figure 3:
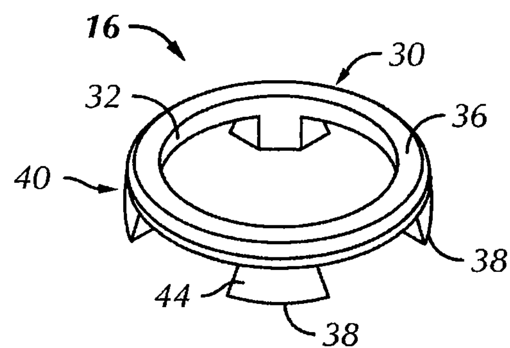
FIG. 3 is a perspective view of a base of the present invention as shown in FIGS. 1 and 2.
Figure 4:
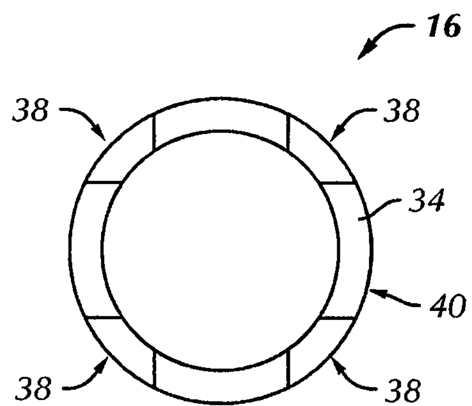
FIG. 4 is a bottom view of the base.
Figure 5:
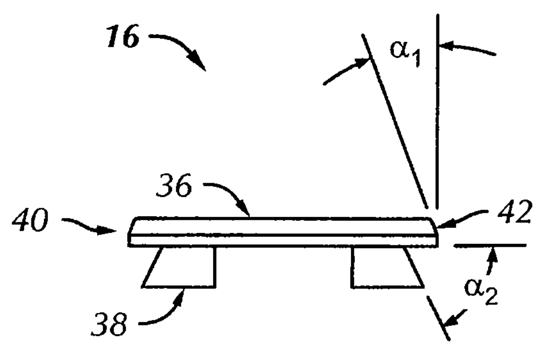
FIG. 5 is a side view of the base.

FIG. 3 is a perspective view of the base. The base includes an annular ring-shaped portion 30 having an upper side 32 and a lower side 34. The upper side includes a donor cornea receiving surface 36. The lower side includes a plurality of legs 38 depending there from. The legs are spaced apart from one another to provide adequate circulation of a fluid preservation media. The annular ring-shaped portion includes a periphery 40 having a beveled side wall 42. The legs are spaced inwardly away from the periphery of the annular ring-shaped portion. The external wall 44 of the legs is shown to be beveled, extending downwardly and outwardly to provide a larger footprint for stability.

Figure 6:
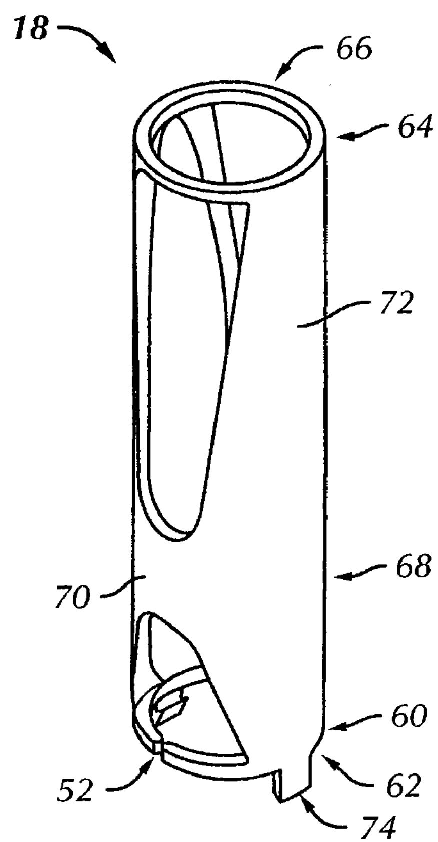
FIG. 6 is a perspective view of the combination clamp and handle of the present invention as shown in FIGS. 1 and 2.
Figure 7:
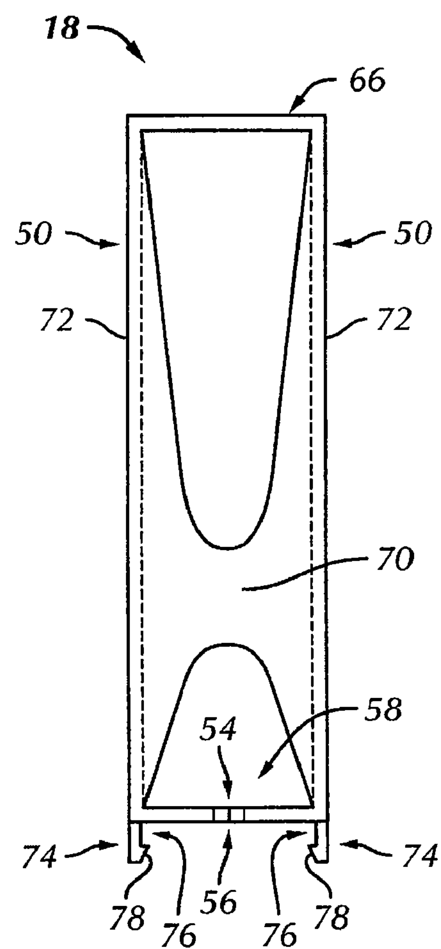
FIG. 7 is a side view of the combination clamp and handle of FIG. 6.

FIG. 6 shows a perspective view of the clamp 18. The clamp defines a generally cylindrical shape. FIG. 7 shows the clamp includes two opposing handles or levers 50 which extend in a direction parallel to the longitudinal axis of the clamp. The lower end of the clamp includes a split ring-shaped clamp 52. The split ring-shaped clamp includes an upper side 54 and a lower side 56. The lower side of the split ring-shaped clamp provides a cornea mating or receiving surface 58. Each lever includes a proximal end 60 secured to a respective portion 62 of the split ring-shaped clamp. The distal end 64 of the levers are secured together by a stabilizing mechanism in the form of a ring 66. A portion 68 of each lever between the distal and proximal ends are connected together by means of a first and second web portion 70. FIG. 6 shows one web portion. The other web portion is a mirror image of the web portion shown in FIG. 6. Between the portion 68 and distal end 64 is an upper side wall 72. The proximal end of the handles extend further away from the distal ends and form a locking flange 74. FIG. 7 shows that each locking flange includes an under cut 76 with respectively define an abutment surface 78 which extends in a plane perpendicular to the longitudinal axis of the clamp. The clamp shown in FIG. 6 is made of a resilient material.

Figure 8:
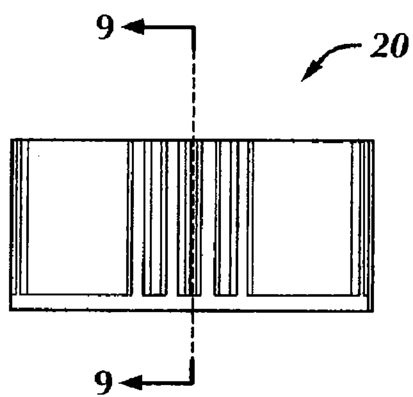
FIG. 8 is a side view of the lid of the present invention as shown in FIGS. 1 and 2.
Figure 9:
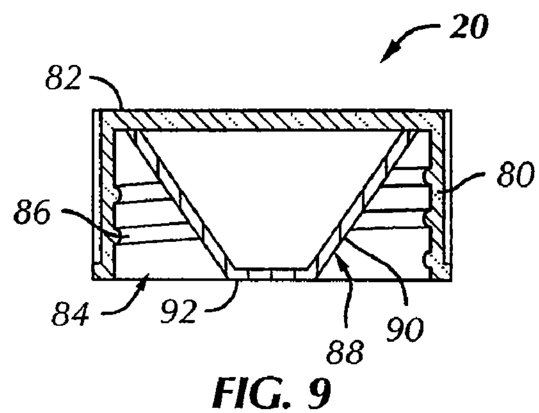
FIG. 9 is a cross-sectional view of the lid of FIG. 8.
Figure 10:
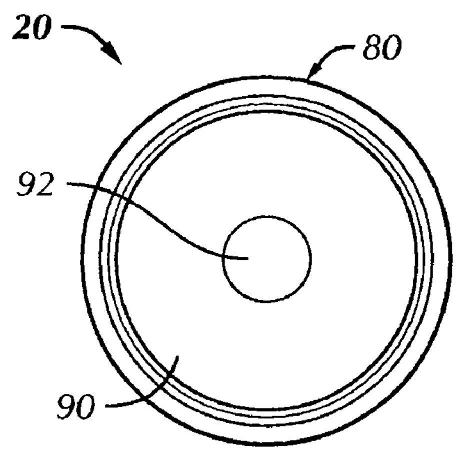
FIG. 10 is a bottom view of the lid of FIG. 8.

FIG. 8 is a side view of the lid. FIG. 9 is a cross-sectional view of the lid of FIG. 8. FIG. 9 shows that the lid includes a cylindrical wall 80 and end cap 82 defining an interior compartment 84. The interior compartment includes a thread 86 extending along the cylindrical wall. A conical shaped portion 88 extends from the end cap in a downward direction. FIG. 10 is a bottom view of the lid of FIG. 8 and shows the interior compartment, including the angled, conical wall 90 of the conical shaped portion and the end wall 92 of the conical shaped portion.

In operation, the donor cornea 12 is placed upon the base 16, with the endothelial layer facing the cornea receiving surface 36. The user grasps the clamp at the upper side walls 72 of the clamp. The user presses the upper side walls together thereby causing the clamp to flex and pivot about the web portions 70 causing the split ring-shaped clamp 52 to separate and open. In this configuration, the clamp 18 is placed over the cornea 12 and base 16 with the abutment surfaces 78 extending below the lower side 34 of the base. With the clamp properly oriented with respect to the cornea and base, the pressure is removed from the upper side walls 72, causing the locking flanges 74 to close upon the base with the abutment surfaces 78 coming into contact with the lower side 34 of the base 16. In this manner, the clamp 18 and base 16 securely lock the cornea 12 there between.

The combination clamp base and cornea are then placed into the vial 14 having a fluid preservation media. The legs of the base rest upon the optically clear closed end of the vial. The lid is then threaded onto the open end of the vial, with the conical shaped portion coming into contact with the ring-shaped stabilizing mechanism, thereby securing the clamp and securing the clamp and base between the lid and the closed end of the vial. This arrangement prevents the assembly from moving out of position for viewing in the vertical position for cell counting of the endothelia layer and also in the horizontal position for slit lamp inspection of the cornea.

Later, at point of use, the lid is removed from the vial and the assembly is removed from the vial and placed on its feet in the sterile field. At this time, the flexible upper side walls of the levers are squeezed inward to remove the locking feature of the locking flanges and allowing the removal of the clamp. The donor cornea is now resting on the base of the unit with the endothelial side of the cornea fully protected and not in contact with any surface. The corneal-scleral unit is now available for use in the transplant procedure.

The apparatus of the present invention secures the donor cornea in a vial for ease of access and to allow removal of the donor cornea without risk of damage to the donor cornea. The fixture allows for optical examination without removing the donor cornea from the vial. The fixture also allows for easy and safe retrieval of the donor cornea by the transplant surgeon. This eliminates risk of damage and eliminates the need to transfer the donor cornea into a fresh vial of preservation media.

Figure 16:
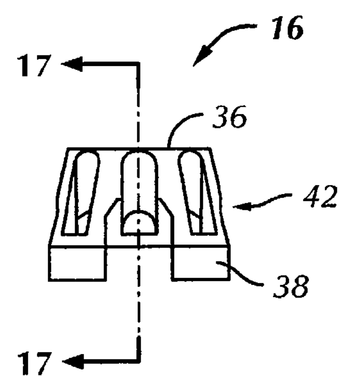
FIG. 16 is a perspective side view of the base of FIG. 11.
Figure 14:
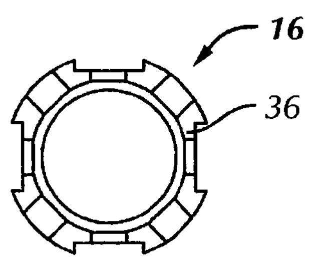
FIG. 14 is a top view of the base, of FIG. 11.
Figure 17:
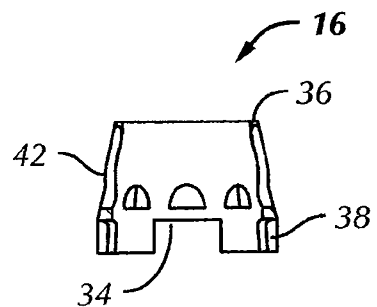
FIG. 17 is a side cross section view of the base taken along line 17-17 of FIG. 16.
Figure 18:
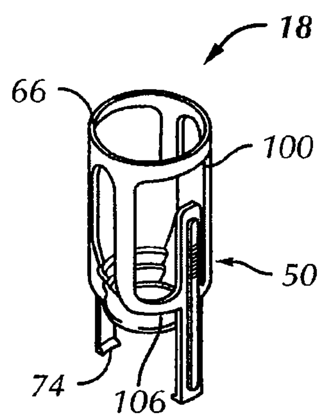
FIG. 18 is a perspective view of the clamp of FIG. 11.

FIGS. 11-22 show another embodiment. Features which are similar to those of the first embodiment are identified with the corresponding reference numeral. FIG. 16 shows that the leg or legs 38 of the base 16 are essentially an extension of the beveled side wall 42. It will be appreciated that the embodiment of FIGS. 11-22 provide greater stability than the embodiment of FIGS. 1-10. It will also be appreciated from FIGS. 11-22, particularly from FIGS. 11 and 12, that the further embodiment raises the cornea receiving surface 36 a greater distance from the end 24 of the vial 14, in comparison to the first embodiment. Thus, the cornea is elevated from suspended particulate which may collect or accumulate at or near the end 24, with the vial 14 in the upright position.

Figure 20:
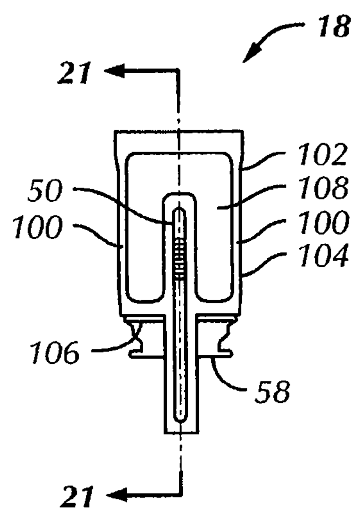
FIG. 20 is a second side view of the clamp of FIG. 18, but taken along the line 20-20 of FIG. 19.
Figure 19:
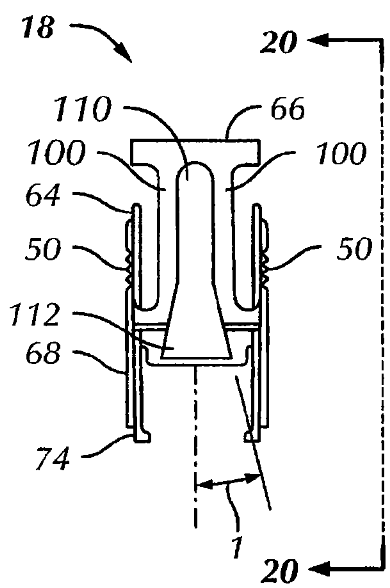
FIG. 19 is a first side view of the clamp of FIG. 18.
Figure 21:
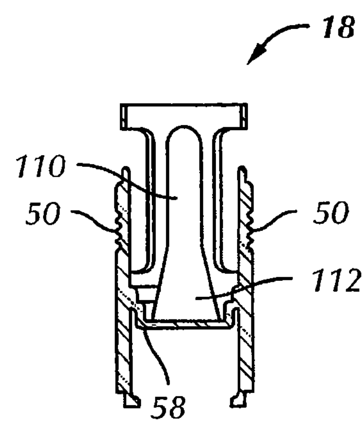
FIG. 21 is a side cross section view of the clamp of FIG. 18 taken along line 21-21 of FIG. 20.
Figure 22:
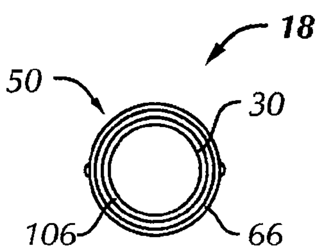
FIG. 22 is a top view of the clamp of FIG. 11.

FIGS. 18-21 show that the distal end 64 of the handles or levers 50 do not extend up to ring 66. The distal ends 64 stop short of the ring 66. Instead, four structures 100 extend downwardly from the ring 66 from a first end 102. The second end 104 of the structures 100 connect to the cornea mating surface 58 via a stepped web portion 106 extending from either side of the handles or levers 50. FIG. 20 shows that the two structures 100 which connect at either side of a respective lever 50 are spaced apart from one another and the respective lever 50. An opening 108 is defined by the two structures 100 shown in FIG. 20. FIGS. 19 and 21 show that two structures 100 which connect to opposing levers 50, define an opening 110 having an enlarged cutout 112 which extends downward to the cornea mating surface 58. The combination clamp and handle 18 of FIGS. 11-22 is designed to enhance a bellow like compression upon securing the lid 20 to the vial 14, with the downwardly movement of the conical wall 90 upon the ring 66. Extended arms 114 of the levers 50 include the locking flange 74 and operate independent from the compression action of the structures 100 and stepped web portion 106.

Figure 11:
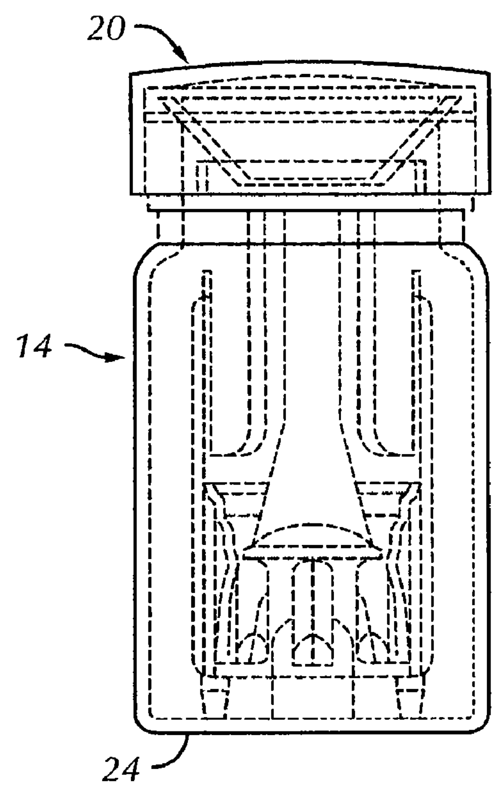
FIG. 11 is a perspective view of the apparatus containing a donor cornea, in accordance with a further embodiment of the present invention.
Figure 12:
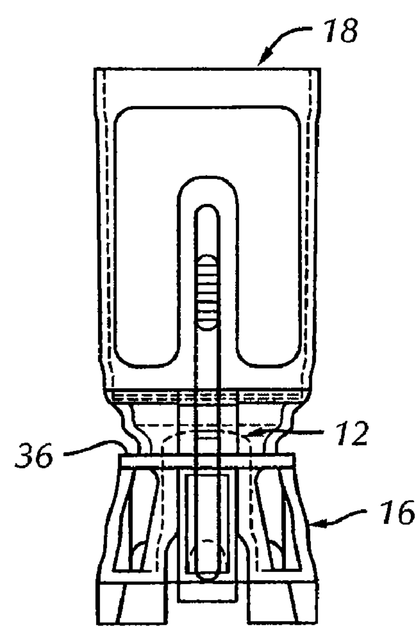
FIG. 12 is a perspective view of the platform and clamp of FIG. 11, with the donor cornea in place.
Figure 15:
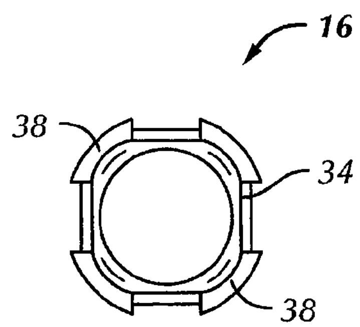
FIG. 15 is a bottom view of the base of FIG. 11.
Figure 13:
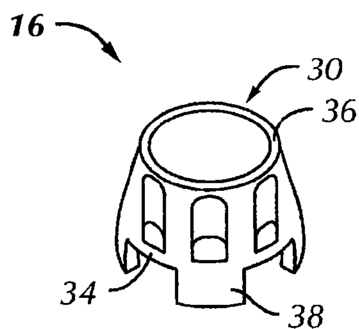
FIG. 13 is a perspective view of a base or platform of the present invention as shown in FIGS. 11 and 12.

With reference particularly to FIGS. 1 and 11, it will be appreciated that, in one embodiment, the dimension of the fixture and vial are selected to provide a focal length appropriate for a microscope viewing the cornea 12 through the end 24 of the vial 14.

The invention claimed is:

1. An apparatus for the in vitro storage of a cornea, the apparatus comprising:

a platform having a top side and a bottom side, the top side having a cornea receiving surface, wherein the receiving surface is a ring having an annular perimeter and legs extending from the bottom side of the platform;

a clamp having a top side and a bottom side, the clamp bottom side including a cornea mating surface, wherein the clamp is generally cylindrical in profile and includes a split ring having a first and second ring half which provides the cornea mating surface, the split ring defining an outer periphery;

a platform and clamp locking mechanism; and a storage unit for placement of the clamp, platform and locking mechanism.

2. The apparatus of claim 1 wherein the storage unit includes a stabilizing mechanism.

3. The apparatus of claim 1, wherein the clamp further has two levers extending in a direction parallel to the longitudinal axis defined by the cylindrical profile and in an opposed and spaced apart relation from one another, the levers each having a proximal end attached to a respective ring half, the levers each having a distal end, the levers each having a portion between the proximal and distal ends, the respective portions connected to form a pivot connection.

4. The apparatus of claim 3 wherein in a quiescent state, the pivot connection urges the first and second ring halves toward one another.

5. The apparatus of claim 3 wherein the pivot connection is made of a resilient material.

6. The apparatus of claim 1, wherein each ring half includes a locking flange extending parallel to the longitudinal axis and away from the distal end of the levers.

7. The apparatus of claim 6 wherein the receiving surface is a ring having an annular perimeter, the annular perimeter having a beveled portion, the locking flanges providing beveled portions facing each other in a spaced apart relationship.

8. The apparatus of claim 7 wherein the beveled portion of the platform is inclined at a first angle, and the beveled portion of the locking flanges are inclined at a second angle substantially similar to the first angle.

9. The apparatus of claim 6 wherein the locking flanges each includes an under cut which defines an abutment surface traverse to the longitudinal axis, wherein the abutment surfaces are spaced from the clamp mating surface a first distance, and wherein the platform has a thickness substantially equal to the first distance.

10. The apparatus of claim 5 wherein the distal ends of the levers are connected by a stabilizing ring, the storage unit includes a vial having an open end and a closed end, and a lid, the lid including an interior portion having a conical shape portion, the lid being secured to the open end of the vial with the conical shape portion being received by the stabilizing ring.

11. The apparatus of claim 10 wherein the vial has threads at the open end and the lid has threads for mating with the vial threads, wherein the lid is secured to the vial and the conical shaped portion exerts a pressure upon the stabilizing ring to urge the clamp and platform against the closed end of the vial.

12. The apparatus of claim 7 wherein the platform ring includes an outer diameter and an inner diameter, where the outer diameter is in the range of 13-16 mm and the inner diameter is approximately 11 mm.

13. The apparatus of claim 8 wherein the legs extending from the bottom side of the platform are spaced from the periphery of the platform, whereby clearance is provided for the locking flanges.

14. The apparatus of claim 2 wherein the clamp is cylindrically-shaped and the clamp has side portions that include cutaway portions that provide the ability to flex the clamp and allow the movement of preservation media through the clamp.

15. An apparatus for the in vitro storage of a cornea, the apparatus comprising:

a circular support base platform having a top side and a bottom side, the top side having a cornea receiving surface, and the bottom side having legs extending from the bottom side of the platform;

a cylindrically-shaped clamp having a top portion and a bottom portion, the clamp bottom portion including a circular mating surface in the form of a split ring that includes two halves and attached locking flanges for securing the cornea on the receiving surface;

a vial for receiving the clamp and platform, the vial having an open end with external threads;

a lid for securing the open end of the vial, the lid having a cylindrical wall and an open end portion forming an interior compartment, the interior compartment having threads along the cylindrical wall, and a conical shaped portion extending from the end portion, whereby as the lid is threaded onto the vial, the conical shaped portion engages the clamp so as to provide further stability and security for the cornea.

16. The apparatus of claim 15 wherein the receiving surface is a ring.

17. The apparatus of claim 16 wherein the ring includes an outer portion and an inner portion, where the outer portion is sized to accommodate a 13-16 mm diameter cornea and the inner portion allows viewing of a cornea's endothelial layer to a diameter of 11 mm.

18. The apparatus of claim 15 wherein there are four legs.

19. The apparatus of claim 16 wherein the clamp is cylindrically-shaped and the clamp has side portions that include cutaways that provide the ability to flex the clamp and allow the movement of preservation media through the clamp.

20. A fixture for securing a cornea for in vitro storage within a container, the fixture comprising:

a platform having a cornea receiving surface;

a clamp having a cornea mating surface comprising a stepped web portion extending substantially in an annular manner, the stepped web portion providing the cornea mating surface, wherein the clamp includes an upper end and a lower end, the upper end including a ring, the ring having a plurality of support structures, each support structure having a first end and a second end, the first end of each support structure being connected to the ring, with the support structures extending downwardly from the ring toward the lower end of the clamp, the second end of each support structure connecting to the stepped web portion; and a platform and clamp locking mechanism.

21. The fixture of claim 20, wherein the cornea receiving surface forms an annular ring.

22. The fixture of claim 20, wherein the platform includes a plurality of legs which extend downwardly and outwardly.

23. The fixture of claim 20, wherein the platform includes a beveled side wall which extends downwardly and outwardly, and a plurality of legs that extend downwardly and outwardly from the beveled side wall.

24. The fixture of claim 20, wherein the clamp includes a pair of opposed facing levers, each lever having a mid portion coupled to the stepped web portion, an upper end extending upward toward the upper end of the clamp and adjacent the ring, and a lower end ending below the cornea receiving surface, each lower end including a locking flange.

25. The fixture of claim 24, wherein the clamp includes four support structures, wherein an opening is defined between at least one pair of adjacent support structures, the opening extending downward into the stepped web portion adjacent the cornea mating surface.

26. The fixture of claim 20, wherein the clamp includes a compressible mechanism to allow the clamp to compress under a longitudinally imposed external force.

27. The fixture of claim 20, further comprising a stabilizing mechanism for maintaining the position of the fixture within a container.

28. The fixture of claim 20, wherein the platform includes a lower end defined by legs on a base, wherein the length of the base to the cornea receiving surface is selected to provide a focal length required of an examining microscope.

* * * * *

UNITED STATES PATENT AND TRADEMARK OFFICE

CERTIFICATE OF CORRECTION

PATENT NO. : 7,662,611 B2
APPLICATION NO. : 11/259516
DATED : February 16, 2010
INVENTOR(S) : Schmidt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1137 days.

Signed and Sealed this

Thirtieth Day of November, 2010

David J. Kappos
*Director of the United States Patent and Trademark Office*